(12) United States Patent
Tzeng et al.

(10) Patent No.: US 8,580,847 B2
(45) Date of Patent: Nov. 12, 2013

(54) ANTROCIN CONTAINING PHARMACEUTICAL COMPOSITIONS FOR INHIBITING CANCER CELLS

(75) Inventors: Yew-Min Tzeng, Taichung (TW); Tien-Shen Yang, Taichung (TW); Chi-Tai Yeh Yeh, Taipei (TW)

(73) Assignee: Chaoyang University of Technology, Taichung County (TW)

( * ) Notice: Subject to any disclaimer, the term of this patent is extended or adjusted under 35 U.S.C. 154(b) by 45 days.

(21) Appl. No.: 13/337,681

(22) Filed: Dec. 27, 2011

(65) Prior Publication Data

US 2012/0100175 A1    Apr. 26, 2012

Related U.S. Application Data

(63) Continuation-in-part of application No. 12/767,754, filed on Apr. 26, 2010, now abandoned.

(51) Int. Cl.
| | |
|---|---|
| *A01N 43/08* | (2006.01) |
| *A01N 43/16* | (2006.01) |
| *A01N 65/00* | (2009.01) |
| *A61K 31/34* | (2006.01) |
| *A61K 31/35* | (2006.01) |
| *A61K 36/06* | (2006.01) |
| *A61K 36/09* | (2006.01) |

(52) U.S. Cl.
USPC ............... 514/468; 514/453; 424/195.15

(58) Field of Classification Search
USPC ................... 514/468, 453; 424/195.15
See application file for complete search history.

(56) References Cited

U.S. PATENT DOCUMENTS

2006/0251673 A1* 11/2006 Hwang et al. ............ 424/195.15

OTHER PUBLICATIONS

Chiang et al. Phytochemistry, 1995, vol. 39, No. 3, pp. 613-616.*
Yan et al. J. Chromatogr. A, 2004. vol. 1043, pp. 329-332.*
Rao et al. Chemical Research in Toxicology, Published online 2010, vol. 24, No. 2, pp. 238-245.*

* cited by examiner

*Primary Examiner* — Samira Jean-Louis
(74) *Attorney, Agent, or Firm* — WPAT, P.C.; Anthony King

(57) ABSTRACT

This subject invention is directed to a method for inhibition of cancer cells, comprising administrating an effective amount of a compound of formula I (Sesquiterpene lactones, antrocin) or pharmaceutically acceptable salts thereof, together with a pharmaceutically acceptable carrier, wherein the cancer cells are selected from colorectal cancer cells, liver cancer cells, lung cancer cells or breast cancer cells.

3 Claims, 4 Drawing Sheets

ANTROCIN CONTAINING PHARMACEUTICAL COMPOSITIONS FOR INHIBITING CANCER CELLS

CROSS-REFERENCE TO RELATED APPLICATIONS

This application is a Continuation-in-part of the pending U.S. patent application Ser. No. 12/767,754 filed on Apr. 26, 2010, for which priority is claimed and is incorporated herein by reference in its entirety.

Although incorporated by reference in its entirety, no arguments or disclaimers made in the parent application apply to this Continuation-in-part application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

This invention relates to a method for inhibition of cancer cells, comprising administrating an effective amount of formula I (Sesquiterpene lactones, antrocin) or a pharmaceutically acceptable salt thereof, together with a pharmaceutically acceptable carrier, wherein the cancer cells are selected from colorectal cancer cells, liver cancer cells, lung cancer cells or breast cancer cells.

BACKGROUND OF THE INVENTION

Cancer is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Cancer affects people at all ages with the risk for most types increasing with age.

Cancer is invasive and tends to metastasize to new sites. It spreads directly into surrounding tissues and also may be disseminated through the lymphatic and circulatory systems. Many treatments are available for cancer, including surgery and radiation for localized disease, and drugs. However, the efficacy of available treatments on many cancer types is limited, and new, improved forms of treatment, especially the development of searching new natural compounds and/or chemically synthesized compounds for chemotherapy are needed. This is especially true for those patients presenting with advanced and/or metastatic disease. It is also true for patients relapsing with progressive disease after having been previously treated with established therapies for which further treatment with the same therapy is mostly ineffective due to acquisition of resistance or to limitations in administration of the therapies due to associated toxicities.

SUMMARY OF THE INVENTION

Figure 1:
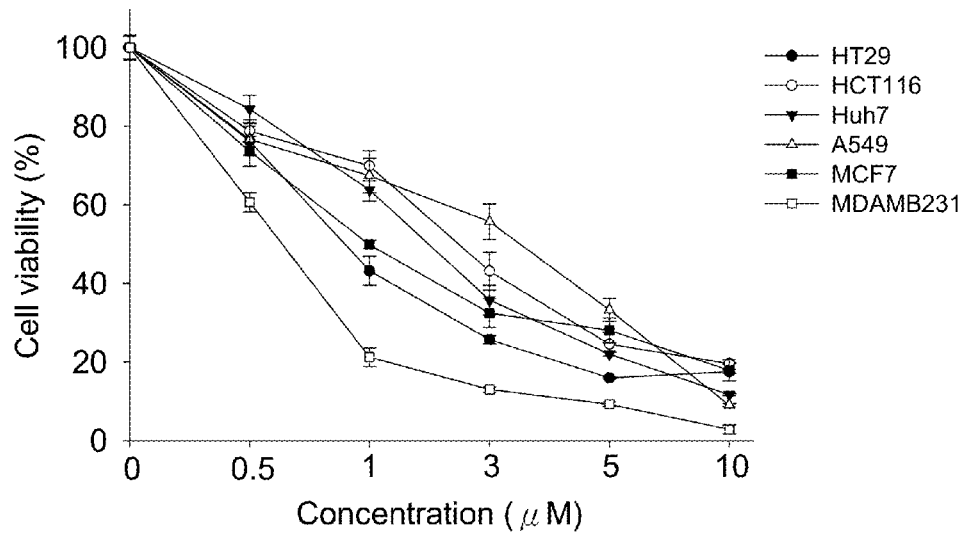
FIG. 1 shows the effect of antrocin on the growth of various human cancer cells. Relative cell viability (%)=O.D. value (A562nm, antrocin)/O.D. value (A562 nm, control)×100%.

This invention relates to a method for inhibition of cancer cells, comprising administrating an effective amount of formula I (Sesquiterpene lactones, antrocin) or a pharmaceutically acceptable salt thereof, together with a pharmaceutically acceptable carrier, wherein the cancer cells are selected from colorectal cancer cells, liver cancer cells, lung cancer cells or breast cancer cells.

DETAILED DESCRIPTION OF THE INVENTION

This subject invention is directed to a pharmaceutical composition for the inhibition of cancer cells, particularly breast cancer cells, comprising an effective amount of a compound of formula I (Sesquiterpene lactones, antrocin) or pharmaceutically acceptable salts thereof, together with a pharmaceutically acceptable carrier. Accordingly, the present invention relates to a pharmaceutical composition for treating or preventing cancer by inhibiting cancer cell growth comprising a therapeutically effective amount of antrocin or a pharmaceutically acceptable salt thereof, and a pharmaceutically acceptable carrier.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The present invention relates to a pharmaceutical composition for treating or preventing cancer by inhibiting cancer cell growth. Formula I-antrocin showed high inhibition activity to different cancer cell lines including colorectal cancer cell line—HT-29 or HCT116, liver cancer cell line—Huh7, lung cancer cell line—A549 and breast cancer cell line—MCF7 or MDA-MB-231. However, Formula I-antrocin had almost no cell toxicity to normal cells including foreskins fibroblast cells and non-tumorgenic breast epithelial cells. Experimentally, formula I-antrocin has been found to have exceedingly high activity on inhibiting MDA-MB-231 human breast carcinoma cell growth comparing to two other clinical cancer chemotherapy drugs Doxorubicin and Cisplatin with the same dosage.

Formula I-antrocin has one or more chiral centers and therefore has different types of stereoisomer. The term "formula I" as used herein refers to all types of stereoisomer inclusively. Formula I-antrocin inhibits cancer cell growth selectively. Low molecular weight allows formula I-antrocin or a pharmaceutically acceptable salt therein, and a pharmaceutically acceptable carrier to be used in a low dosage to achieve the desirable inhibition effect on cancer cell growth.

As used herein, a "pharmaceutically acceptable" component (such as a salt, carrier, excipient or diluent) means that the compound or composition is suitable for administration to a subject to achieve the inhibition of cancer cells described herein, without unduly deleterious side effects in light of the severity of cancer and necessity of the treatment.

As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc). Compositions comprising such carriers are formulated by well known conventional methods. Depending on the intended mode of administration and the intended use, the compositions may be in the form of solid, semi-solid, or liquid dosage forms, such, for example, as powders, granules, crystals, liquids, suspensions, liposomes, pastes, creams, salves, etc., and may be in unit-dosage forms suitable for administration of relatively precise dosages.

"An effective amount" as used herein refers to an amount necessary to inhibit cancer cell growth. An effective amount differs according to the administration route, excipient usage and co-usage of other active agents.

Formula I—antrocin can be extracted from the fruiting bodies of Antrodia camphorata which usually grows on the wood section of bull camphor tree 〖 Cinnamomum kanehirae Hayata (Lauraceae)〗 with solvent under reflux and purified by silica gel column chromatography afterwards. It can also be prepared by chemical synthesis methods.

"A. camphorata grows on bull camphor tree" as used herein refers to extract got from A. camphorata with an appropriate growth level. The extraction method has its understood meaning in the art, for example, soaking the ground and dried A. camphorata fractions into mixture comprising a solvent or two or more solvents for an appropriate period. In particular embodiments, exemplary solvents include, but not limited to, water, methanol, ethanol, methylene chloride, chloroform, acetone, ether (i.e., diethyl ether), ethyl acetate and hexane. The A. camphorata extract solution is obtained after removing the solid residues and is purified by silica gel column chromatography to yield formula I—antrocin.

The list of bioactivities of crude extracts of A. camphorata is huge, ranging from anti-cancer to vasorelaxation and others. Over 78 compounds consisting of terpenoids, benzenoids, lignans, benzoquinone derivatives, succinic and maleic derivatives, in addition to polysaccharides have been identified (Geethangili and Tzeng, 2009). The bitter components of A. camphorata are triterpenoids and have known pharmacological activities. Triterpenes are considered to be potential anti-cancer agents due to their activity against growing tumors and direct cytotoxicity against tumor cells rather than to normal cells. However, clinical trails of human on triterpenes are limited because they need to be used under modest higher concentration to achieve the desirable treatment effect like chemotherapy drugs.

Formula I—antrocin is first reported the isolation from the fruiting bodies of A. camphorata in 1995 (Chiang et al,. 1995). However, due to low content of formula I—antrocin in A. camphorata and difficulty in extraction, there has been no further formula I-antrocin related report during the past 15 years.

Formula I—antrocin of the present invention is extracted from A. camphorata with an appropriate growth level. It is extracted from the fruiting bodies of A. camphorata with solvent under reflux and purified by silica gel column chromatography afterwards.

The present invention relates to a pharmaceutical composition for treating or preventing cancer by inhibiting cancer cell growth. Formula I-antrocin showed high inhibition activity to different cancer cell lines including colorectal cancer cell line—HT-29 or HCT116, liver cancer cell line—Huh7, lung cancer cell line—A549 and breast cancer cell line—MCF7 or MDA-MB-231. However, formula I-antrocin had almost no cell toxicity to normal cells including foreskins fibroblast cells and non-tumorgenic breast epithelial cells. Experimentally, formula I-antrocin has been found to have exceedingly high activity on inhibiting MDA-MB-231 human breast carcinoma cell growth comparing to two other clinical cancer chemotherapy drugs Doxorubicin and Cisplatin with the same dosage. It is noteworthy that, among all kinds of natural compounds in A. camphorata, formula I-antrocin is the only experimentally confirmed compound having higher activity on inhibiting cancer cells than clinical cancer chemotherapy drugs Doxorubicin or Cisplatin do, respectively.

Furthermore, the effective cancer cells inhibition amount of the formula I-antrocin of the present invention is from 0.01 µM to 1000 µM, preferably from 0.5 µM to 50 µM.

This invention further relates to a method for inhibition of cancer cells, comprising administrating an effective amount of formula I (Sesquiterpene lactones, antrocin) or a pharmaceutically acceptable salt thereof, together with a pharmaceutically acceptable carrier, wherein the cancer cells are selected from colorectal cancer cells, liver cancer cells, lung cancer cells or breast cancer cells.

EXAMPLES

Example 1

Extraction and Isolation of Antrocin

The compound antrocin was purified and identified from the fruiting bodies of A. camphorata. Briefly, the air-dried powder of the fruiting bodies was successively extracted with methanol under reflux. After exhaustive extraction, the methanol extracts were concentrated under reduced pressure. The $CHCl_3$ soluble fraction was chromatographed over silica gel using n-hexane/EtOAc gradient eluent, and similar fractions were combined to produce many fractions. Active fraction was purified by silica gel column chromatography using $CHCl_3$/MeOH to yield antrocin. The purity of the antrocin was assessed by HPLC analysis.

Example 2

Biological Assay

1. Freezing and Thawing Cultured Cells

Remove vial of frozen cells from the nitrogen freezer and transfer to a 37° C. heat block (or the incubator) to thaw (thawing generally takes only 1-2 minutes). Clean outside of tube with alcohol before opening. Although you can spin down the thawed cells, resuspend them, and add thawed cells to ~20 ml of chilled fresh medium.

2. Cell Lines and Culture

MCF-7 and MDA-MB-231 breast tumor cell lines came from a pleural effusion of patients with invasive breast carcinoma. The MCF-10A cell line is a non-tumorigenic epithelial cell line. All three human cell lines were provided by the American Type Culture Collection (ATCC). In the present invention, MDA-MB-231 cells were grown in Dulbecco's Modified Eagle's Medium (DMEM) media with 10% FBS, 2 mM glutamine, 100 μg/ml streptomycin in a 37° C. humidified atmosphere with $CO_2$. MCF-7 were cultured in DMEM media supplemented with 2 mM L-glutamine, 100 μg/ml streptomycin, 10% fetal bovine serum, 0.04 UI/ml insulin in a humidified atmosphere at 37° C. containing 5% $CO_2$. MCF10A cells were maintained in DMEM containing 5% horse serum, 2 mM L-glutamine, 20 μg/ml gentamycin, 20 ng/ml epidermal growth factor, 100 ng/ml cholera toxin, 0.25 UI/ml insulin and 0.5 μg/ml hydrocortisone held at 37° C. with 5% $CO_2$.

3. Antrocin Exposure

Antrocin was dissolved in DMSO at a concentration of 10 mM and was stored in a dark-colored bottle at −20° C. as a stock solution. The stock was diluted to the required concentration with serum-free medium immediately before use. Before treatment with antrocin, the medium was removed when cells were about 70% confluent, the cells were starved overnight in serum-free medium and then exposed to antrocin at different concentrations (0-10 μM) and for different periods of time (0-48 h).

4. Cytotoxicity Assay

Briefly, three breast cancer cells (MDA-MB-231, MCF-7 & MCF-10A) were seeded into 96-well plates in growth medium at 3000 cells/well for 24 h. Then, the cells were treated with antrocin at various concentrations (0, 0.5, 1, 3, 5 and 10 μM) for various periods of time. After the exposure period, the cells were fixed with TCA for 1 hour and stained with 100 μL of 0.4% (w/v) SRB for 10 minutes at room temperature. The bound dye was solubilized in 20 mM Tris base (100 μL/well) for 5 minutes on a shaker. Optical densities were read on a microplate reader (Molecular Devices, Sunnyvale, Calif.) at 562 nm.

5. Cell Morphology Studies

After treatment with different dose of antrocin for 48 hr, the MDA-MB-231 cells, cultured on glass coverslips, were washed three times with PBS, fixed with 3% paraformaldehyde for 10 min at room temperature, and then washed in PBS again, and the morphological changes were observed. Cell morphology was then observed by phase microscopy.

6. Cell Cycle Analysis

A total of $2 \times 10^5$ MDA-MB-231 cells/dish were seeded onto each 60 mm dish and incubated for 24 h. Various concentration of antrocin were added to the culture media, and the cells were incubated for an additional 48 hr. Cells were harvested and fixed in cold 75% ethanol at 4° C. for 16 h and incubated with 20 μg/ml RNase A at 37° C. for 30 min and then with 40 μg/ml propidium iodide (PI) at 4° C. for 30 min. Samples were immediately analyzed with a FACSCalibur flow cytometer (Becton, Dickinson and Co., San Jose, Calif). Approximately 10,000 counts were made for each sample. The percentage distributions of apoptotic cells were calculated by CellQuest™ software (Becton, Dickinson and Co., San Jose, Calif.).

RESULTS

1. Effect of Antrocin on the Growth of Human Cancer Cells and Normal Cells

Figure 2:
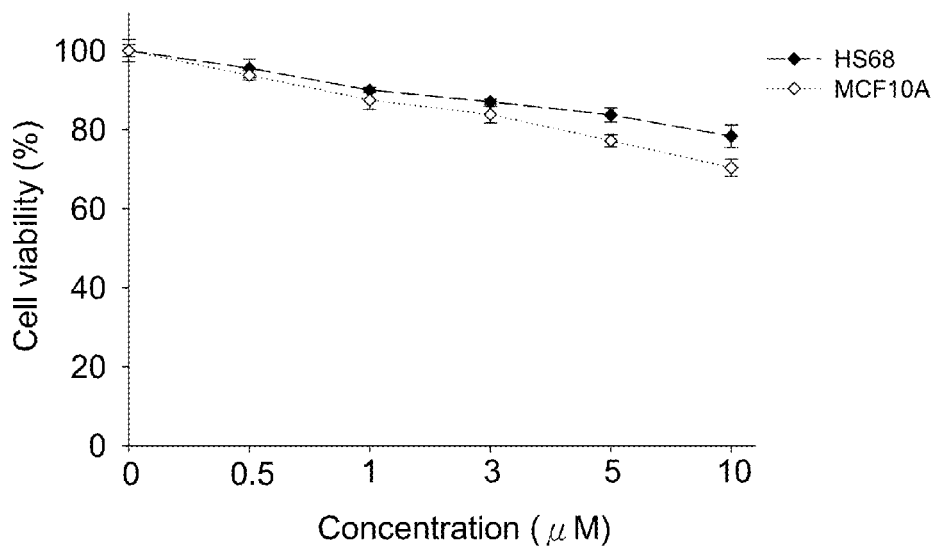
FIG. 2 shows the effect of antrocin treatment on growth of normal foreskins fibroblast HS68 cells and non-tumorgenic breast epithelial MCF10A cells. Relative cell viability (%)=O.D. value (A562 nm, antrocin)/O.D. value (A562 nm, control)×100%.

The anti-proliferative effects of antrocin were assessed on human cancer cell lines, using the SRB assay, with normal foreskins fibroblast HS68 cells and non-tumorgenic breast epithelial MCF-10A cells as controls. As shown in FIG. 1, growth of all of the cancer cells tested was inhibited in a concentration-dependent manner by antrocin. The estimated $IC_{50}$ determined for antrocin in these cancer cell lines ranged from 0.6~4.5 μM, particularly in conditions where an antrocin concentration of 0.5 μM significantly inhibited the MDA-MB-231 cell growth. Interestingly, antrocin had no antiproliferative effect on normal foreskins fibroblast HS68 cells and non-tumorgenic breast epithelial MCF-10A cells (FIG. 2).

2. Comparative in vitro Cytotoxicity of Antrocin, Doxorubicin and Cisplatin against MDA-MB-231

Figure 3:
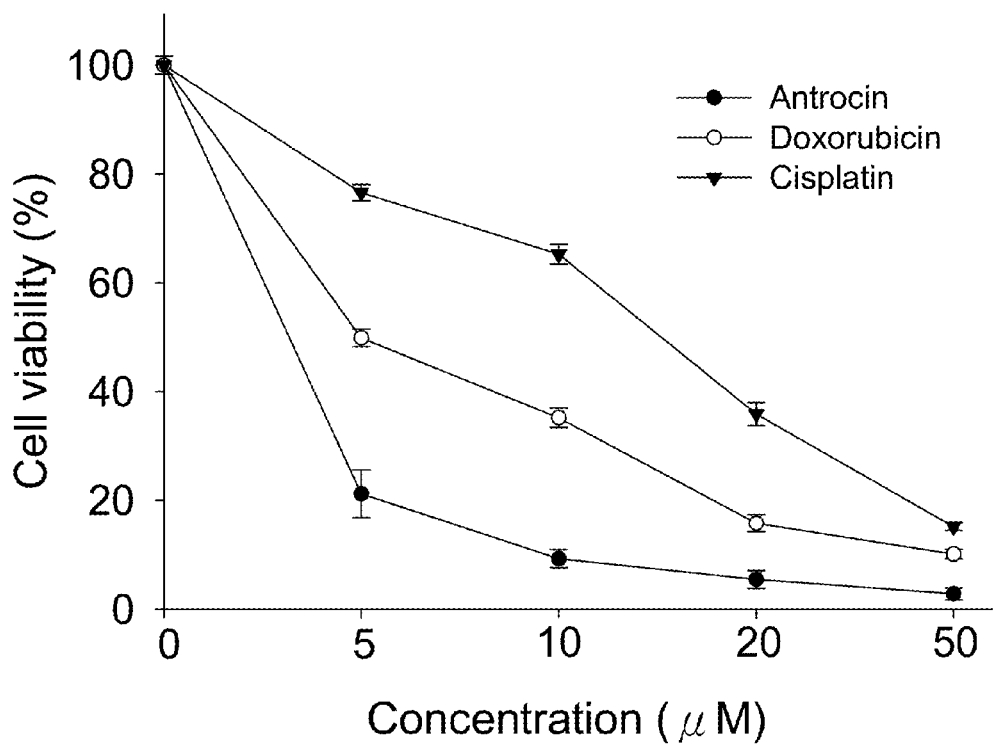
FIG. 3 shows that antrocin was found to be more potent than doxorubicin or cisplatin in cell growth inhibition in MDA-MB-231 human breast cancer cells. Relative cell viability (%)=O.D. value (A562nm, antrocin)/O.D. value (A562 nm, control)×100%.

Doxorubicin and cisplatin are the commonly used anti-breast cancer drugs. Serious side effects have been reported with the use of doxorubicin and cisplatin including: allergic reactions, severe heart damage with prolonged use, decreased bone marrow function and blood problems. We further comparison the cytotoxicity of antrocin with other clinical chemotherapeutic drugs. As shown in FIG. 3, antrocin was found to be more potent than doxorubicin or cisplatin in cell growth inhibition in MDA-MB-231 cells after 48 hr treatment.

3. Antrocin can Selectively Suppress Breast Cancer Cell Growth

Antrocin was further evaluated for its cytotoxicity against MCF-7, MDA-MB-231 (human breast carcinoma) cells and MCF-10A (non-tumorgenic breast epithelial cells).

The growth inhibitory effects of antrocin on cell population growth in breast cancer cells were determined by SRB assay. Antrocin was found to be more effective in MDA-MB-231 cells in comparison with MCF-7 in cell growth inhibition as observed, but there was no significant inhibition on MCF-10A normal breast cells. The results showed that antrocin selectively inhibits growth of highly aggressive MDA-MB-231 breast cancer cells.

4. Effect of Antrocin on Cell Morphology in MDA-MB-231 Cells

Figure 4:
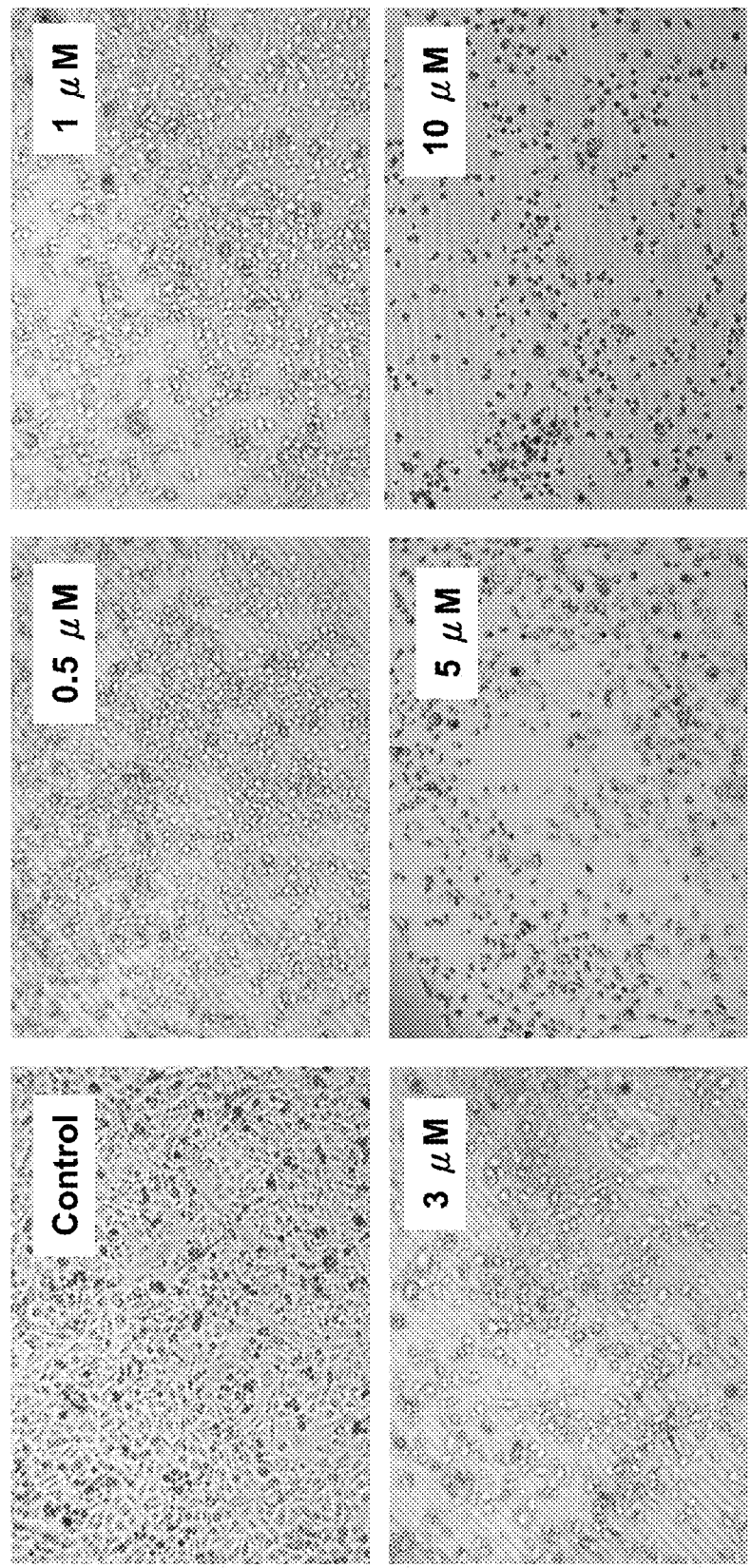
FIG. 4 shows the analysis of morphology changes resulting from antrocin treatment of MDA-MB-231 human breast cancer cell.

The MDA-MB-231 cells were incubated with antrocin, and their morphological alterations were verified via a phase-contrast microscope. As shown in FIG. 4, after 48 hr of incubation with various concentration of antrocin, many cells exhibited cell shrinkage, membrane blebbing, apoptotic body formation and either detached from each other or floated in the medium.

5. Effect of Antrocin on Cell Cycle Distribution

Figure 5:
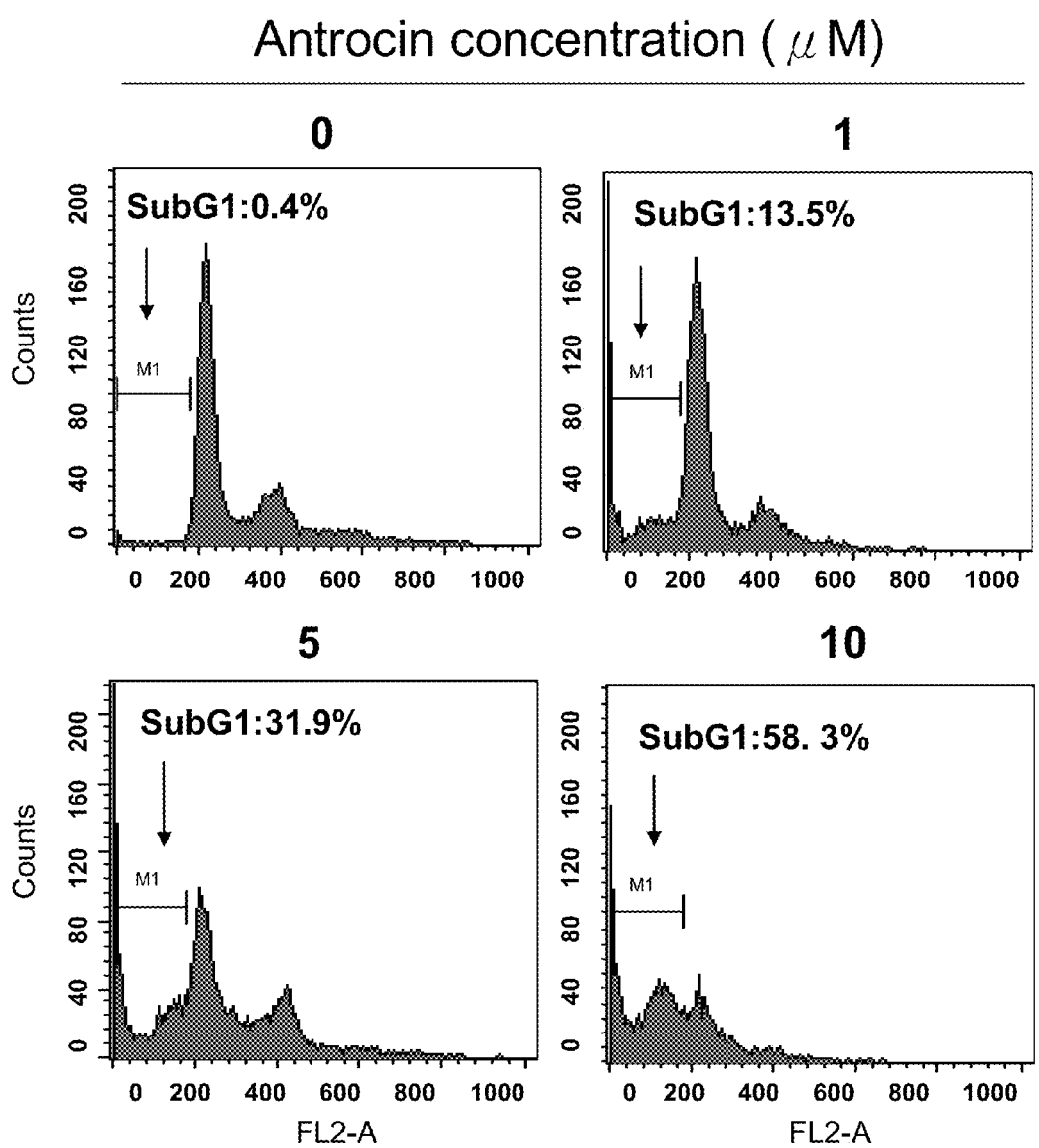
FIG. 5 shows that antrocin induced cell cycle arrest and apoptosis.

To further investigate the effect of antrocin on cell cycle distribution, the DNA content of the MDA-MB-231 cells nuclei was measured using flow cytometry. MDA-MB-231 cells cultured with different dose of antrocin for 48 hr, were washed, stained with the PI, and the cell cycle was performed. As shown in FIG. 5, untreated cells exhibited the expected pattern for continuously growing cells, whereas cells treated with antrocin accumulated progressively in subG1 phase. Furthermore, eventual progression to apoptosis was first observed after 48 hr (58.3%) at 10 μM antrocin treatment. Accordingly, treatment with antrocin induces subG1 accumulation and apoptosis of MDA-MB-231 cells.

What is claimed is:

1. A method for growth inhibition of cancer cells, comprising administering an effective amount of a compound of formula I—antrocin

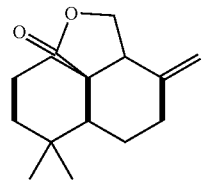

formula I or a pharmaceutically acceptable salt thereof, together with a pharmaceutically acceptable carrier, wherein the cancer cells are selected from colorectal cancer cells, liver cancer cells, lung cancer cells or breast cancer cells.

2. The method of claim 1, wherein the formula I—antrocin is extracted from fruiting bodies of *Antrodia camphorata* with solvent under reflux and purified by silica gel column chromatography.

3. The method of claim 1, wherein the effective amount of the compound of formula I—antrocin is a concentration of 0.5 to 50 µM for cancer cells inhibition.

* * * * *